United States Patent [19]

Agrawal et al.

[11] Patent Number: 5,912,332
[45] Date of Patent: Jun. 15, 1999

[54] AFFINITY-BASED PURIFICATION OF OLIGONUCLEOTIDES USING SOLUBLE MULTIMERIC OLIGONUCLEOTIDES

[75] Inventors: Sudhir Agrawal; Ivan Habus, both of Shrewsbury; Ekambar R. Kandimalla, Worcester, all of Mass.

[73] Assignee: Hybridon, Inc., Milford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,300

[22] Filed: Jul. 26, 1996

[51] Int. Cl.$^6$ .............................. C07H 21/00; C12Q 1/68
[52] U.S. Cl. ...................... 536/23.1; 536/24.3; 536/24.5; 536/25.4; 435/6
[58] Field of Search .................................. 536/23.1, 24.3, 536/24.5, 25.4; 435/6

[56] References Cited

U.S. PATENT DOCUMENTS

| | | | |
|---|---|---|---|
| 5,171,264 | 12/1992 | Merrill | 623/3 |
| 5,321,131 | 6/1994 | Agrawal et al. | 536/25.34 |
| 5,359,047 | 10/1994 | Donahue et al. | 536/23.5 |
| 5,386,020 | 1/1995 | Seeman et al. | 536/23.1 |
| 5,510,471 | 4/1996 | Lebrun et al. | 536/23.4 |
| 5,536,821 | 7/1996 | Agrawal et al. | 536/22.1 |
| 5,543,507 | 8/1996 | Cook et al. | 536/23.1 |

FOREIGN PATENT DOCUMENTS

| | | |
|---|---|---|
| 9325707 | 12/1993 | WIPO . |
| 9508002 | 3/1995 | WIPO . |
| 9703997 | 2/1997 | WIPO . |

OTHER PUBLICATIONS

Agrawal and Iyer, *Current Opin. Biotech.* 6, 12–19 (1995). Month of publication data us unavailable.
Agrawal, *Trends in Biotechnol.* 10, 152–158 (May, 1992).
Crooke et al., *Clin. Pharmacol. Ther.* 56, 641–646 (Dec., 1994).
Damha et al., *Nucleic Acids Res.* 18, 3813–3821 (1990 (Issue No. 13). Month of publication data us unavailable.
Gnanou et al., *Makromol. Chem.* 189, 2885–2892 (1988). Month of publication data us unavailable.
Habus et al., *Bioconjugate Chem.* 6, 327–331 (Issue No. 4, Jul./Aug. 1995.
Habus et al., *Bioorganic and Med. Chem. Lett.* 4, 1065–1068 (1994) (Issue No. 8). Month of publication data us unavailable.
Iversen et al., *Antisense Res. Dev.* 4, 43–52 (1994). Month of publication data us unavailable.
Newkome et al., *Aldrichemica Acta* 25, 31–38 (1992) (Issue No. 2). Month of publication data us unavailable.
Nielson et al., *J. Mol. Recognition* 7, 165–170 (1994). Month of publication data us unavailable.
Padmapriya et al., *Antisense Res. Dev.* 4, 185–199 (1994). Month of publication data us unavailable.
Rein et al., *Acta Polymer* 44, 225–229 (1993). Month of publication data us unavailable.

Sen and Gilbert, *Nature* 334, 364–366 (Jul. 28, 1988).
Uhlmann and Peyman, *Chem. Rev.* 90, 543–584 (Jun. 1990).
Zhang et al., *Clin. Pharmacol. Ther.* 58, 44–53 (Issue No. 1, Jul. 1995).
Bianchi et al., "Interaction of a Protein from Rat Liver Nuclei with Cruciform DNA," *The EMBO Journal*, 7(3), 843–849 (Mar. 1988).
Henderson et al., "Telomere G–Strand Structure and Function Analyzed by Chemical Protection, Base Analogue Substitution, and Utilization by Telomerase in Vitro," *Biochemistry*, 29(3), 732–737 (Jan. 23, 1990).
Bianchi et al., "Specific Recognition of Cruciform DNA by Nuclear Protein HMG1," *Science*, 243, 1056–1059 (Feb. 24, 1989).
Bhattacharyya et al., "Model for the Interaction of DNA Junctions and Resolving Enzymes," *J. Mol. Biol.*, 221(4), 1191–1207 (Oct. 20, 1991).
Du et al., "DNA Junctions, Antijunctions, and Mesojunctions," *Biochemistry*, 31(45), 10955–10963 (Nov. 17, 1992).
Fu et al.(I), "DNA Double–Crossover Molecules," *Biochemistry*,32(13), 3211–3220 (Apr. 6, 1993).
Chung et al., "Eukaryotic Topoisomerase II Cleavage of Parallel Stranded DNA Tetraplexes," *Nucleic Acids Research*, 20(8), 1973–1977 (Apr. 25, 1992).
Weisman–Shomer et al., "QUAD, a Protein from Hepatocyte Chromatin That Binds Selectively to Guanine–Rich Quadruplex DNA," *J. Biol. Chem.*, 268(5), 3306–3312 (Feb. 15, 1993).

(List continued on next page.)

*Primary Examiner*—Marian C. Knode
*Assistant Examiner*—L. Eric Crane
*Attorney, Agent, or Firm*—McDonnell Boehnen Hulbert & Berghoff

[57] ABSTRACT

The present invention provides novel compounds and methods for purifying oligonucleotides. The compounds according to the invention are multimeric oligonucleotides comprising a multimerization domain for inducing multimeric oligonucleotide aggregation, a hybridization domain that is complementary to a target oligonucleotide whose isolation is desired, and a linker domain connecting the multimerization domain and the hybridization domain. Other compounds of the invention comprise dendrimers having oligonucleotides with hybridization domains linked thereto.

The methods of the invention comprise contacting the compounds of the invention with a solution containing a target oligonucleotide whose purification is desired. The target oligonucleotide hybridizes to the hybridization domain of the inventive compounds, thereby forming an aggregate. Synthetic failure sequences (N-1, N-2, etc.) and other oligonucleotides not complementary to the hybridization domain do not hybridize with the hybridization domain of the compounds and remain free in solution. Conventional size exclusion chromatography or small pore filter membranes are then used to separate the aggregate (and hence target oligonucleotide) from the other oligonucleotides. The aggregate is denatured and the target oligonucleotide separated once again by size exclusion chromatography or with a small pore filter membrane.

14 Claims, 7 Drawing Sheets

OTHER PUBLICATIONS

Goodlett et al., "Direct Observation of a DNA Quadruplex by Electrospray Ionization Mass Spectrometry," *Biological Mass Spectrometry*, 22, 181–183 (1993).

Rao et al.(I), "Incorporation of 2'–Doexy–6–thioguanosine into G–Rich Oligodeoxyribonucleotides Inhibits G–Tetrad Formation and Facilitates Triplex Formation," *Biochemistry*, 34(3), 765–772 (Jan. 24, 1995).

Fu et al. (II), "Cleavage of Double–Crossover Molecules by T4 Endonuclease VII," *Biochemistry*, 33(13), 3896–3905 (Apr. 5, 1994).

Rao et al. (II), "A Total Synthesis of 2'–Deoxy–9–deazaguanosine (9–Deaza–dG) and its Incorporation into Triple Helix Forming Oligodeoxyribonucleotides with Antiparallel Motif," *Tetrahedron Letters*, 34(42), 6709–6712 (Oct. 15, 1993).

Ecker et al., "Novel Guanosine Quartet Structure Binds to the HIV Envelope and Inhibits Envelope Mediated Cell Fusion," *Nucleosides & Nucleotides*, 14(3–5), 1117–1127 (May–Jul. 1995).

Jonsson et al., "Role of the His–Cys Finger of Maloney Murine Leukemia Virus Integrase Protein in Integration and Disintegration," *J. Virology*, 67(9), 5562–5571 (Sep. 1993).

Brown et al., "Antibodies Specific for the DNA Quadruplex $[d(CGCG_4GCG)_4]$ Isolated From Autoimmune Mice," disclosed at the Symposium of RNA Biology I. RNA–Protein Interactions, Research Triangle Park, NC, Oct. 13–15, 1995, *Nucleic Acids Symposium Series*, vol. No. 33, 134–136 (1995).

Shida et al., "Interactions Between Quadruple–Stranded Oligodeoxyribonucleotides and Drugs," disclosed at Symposium on Nucleic Acids Technology, Nagoya, Japan, Nov. 8–10, 1990, *Nucleic Acids Symposium Series*, vol. No. 22, 79–80 (1990).

1      3'-GGGGGG|TTTTTTTT|GAGAGCGT-5'

2ª

3ᵇ

4ᶜ     5'-CTCTCGCACC CATCTCTCTCCTTCT-3'

5,912,332

AFFINITY-BASED PURIFICATION OF OLIGONUCLEOTIDES USING SOLUBLE MULTIMERIC OLIGONUCLEOTIDES

BACKGROUND OF THE INVENTION

1. Field of the Invention

This invention relates to the field of purification of synthetic oligonucleotides.

2. Summary of the Related Art

Recent advances in the chemical synthesis of nuclease-resistant oligonucleotides (Agrawal, *Trends in Biotechnol* 10, 152 (1992); Agrawal et al., *Opin. Biotechnol.* 6, 12 (1995)), large scale solid phase synthesis (Padmapriya et al., *Antisense Res. Dev.* 185, 4 (1994)), and purification and analytical techniques (*Methods in Molecular Biology*, Vol 20, *Protocols for Oligonucleotides and Analogs* (Agrawal, Ed., Humana Press, Totowa, N.J., 1993); *Methods in Molecular Biology*, Vol 26, *Protocols for Oligonucleotide Conjugates* (Agrawal, Ed., Humana Press, Totowa, N.J., 1994)) have permitted rational design of sequence specific antisense oligonucleotides and their advancement to human clinical trails (Zhang et al., *Clin. Pharmacol. Ther.* 58, 44 (1995); Iversen et al., *Antisense Res. Dev.* 4, 43 (1994); Crooke et al., *Clin. Pharmacol. Ther.* 56, 641 (1994)). Reverse-phase HPLC, ion exchange chromatography, and gel electrophoresis are currently used for oligonucleotide purification. *Methods in Molecular Biology*, Vol. 26, supra.

Conventional methods of purification rely on such oligonucleotide characteristics as charge and hydrophobicity/hydrophilicity. Consequently, such techniques are frequently not well suited for purification of modified oligonucleotides such as methylphosphonates (no charge), 2'-O-alkyl (hydrophobic) substituted oligonucleotides, and other oligonucleotides with modifications that similarly affect the oligonucleotides charge and hydrophobicity/hydrophilicity. Prior art techniques can also be expensive and time-consuming, particularly in large scale operations. Accordingly, new techniques for oligonucleotide purification that obviate these problems are desirable.

SUMMARY OF THE INVENTION

The present invention provides novel multimeric oligonucleotides and their use for the purification of antisense oligonucleotides through complementary base recognition and size exclusion principles. In a particular embodiment, the invention provides compounds and methods for the purification of full length synthetic oligonucleotides from a solution also containing N-1 and other failure sequences generated during synthesis. The oligonucleotides of the invention are of a unique structure that allows them to hybridize specifically with a desired, full-length oligonucleotide and concomitantly form multimer aggregates. The desired oligonucleotide is thereby bound in a multimer aggregate while other undesired oligonucleotides remain in solution. The desired oligonucleotide is then separated and isolated using size-exclusion techniques.

In one aspect of the invention, the oligonucleotides according to the invention have at least three structural features: (1) a multimerization domain, (2) a hybridization domain, and (3) a linker domain. The multimerization domain comprises a sequence of nucleotides that induces interoligonucleotide aggregate formation. The hybridization domain comprises a sequence of nucleotides that is complementary to the 5' end of a synthetic oligonucleotide whose purification is desired. The linker domain comprises a sequence of nucleotides or non-nucleotide chemical moieties and serves both to link the hybridization domain to the multimerization domain as well as space the hybridization domain away from the multimerization domain to allow for simultaneous aggregate formation and hybridization to the target oligonucleotide.

When contacted with a crude solution containing the desired oligonucleotide and other failure sequences generated during synthesis, the hybridization domain hybridizes to the desired ("target") oligonucleotide but not to the failure sequences, which are insufficiently complementary to hybridize to the hybridization domain under the conditions chosen. The multimerization domains concomitantly induce interoligonucleotide aggregation. The target oligonucleotide is bound in the resulting aggregate. Failure sequences remain free in solution and can be separated from the aggregates using standard size exclusion chromatographic techniques. The aggregates bearing the target oligonucleotides are then subjected to conditions that cause the target oligonucleotide to disassociated from the aggregate, and the free target oligonucleotide is isolated from the target-free aggregate by size exclusion chromatographic techniques.

In another embodiment, the present invention provides oligonucleotide dendrimers comprised of a branched chemical core structure chemically linked to oligonucleotides comprising sequences complementary to one or more target oligonucleotides. Oligonucleotide dendrimers according to the invention are used in the same way as the multimeric oligonucleotides to purify a desired oligonucleotide.

Use of the present compounds and methods results in superior purity of the desired oligonucleotide compared to prior art methods. The present invention depends on specific nucleotide base sequence recognition and not on charge or hydrophobicity/hydrophilicity. Accordingly, it is useful regardless of how the oligonucleotide is modified. A concurrent benefit of the present invention is that the multimeric oligonucleotides are reuseable. Thus, it is seen that a problem solved by the present invention is provision of compounds and methods for the improved purification of oligonucleotides.

The foregoing merely summarizes certain aspects of the present invention and is not intended, nor should it be construed, to limit the invention in any way. All patents and other publications recited herein are hereby incorporated by reference in their entirety.

DETAILED DESCRIPTION OF THE PREFERRED EMBODIMENTS

Figure 1:
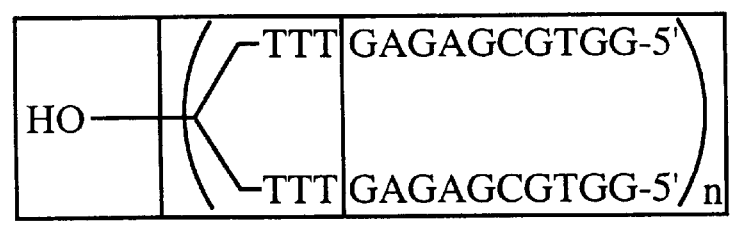
FIG. 1 displays representative oligonucleotides and dendrimers of the present invention.
Figure 1:
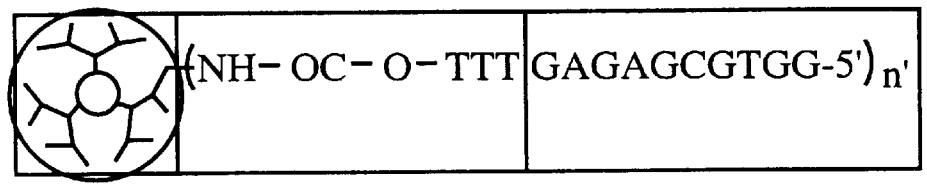

The present invention provides compounds and methods useful for purifying synthetic oligonucleotides. Oligonucleotides are generally synthesized in a stepwise manner, adding one nucleotide (or nucleotide dimer or trimer blocks) at a time to the 5' end of a nascent, solid-support-bound oligonucleotide. Because the reaction that adds each additional nucleotide has less than 100% yield, the final oligonucleotide composition is a mixture of the desired full length oligonucleotide (of "N" nucleotides in length) and failure sequences, which are shorter oligonucleotides, being one or more nucleotides shorter in length. These failure sequences are often referred to as N-1, N-2, etc., oligonucleotides, the number indicating how many fewer nucleotides there are as compared to the full length desired oligonucleotide. Prior art techniques for separating the full length ("target") oligonucleotide from the failure sequences (particularly the N-1 sequence) have met with limited success. The compounds and methods of the present invention provide a substantial improvement over the prior art.

The compounds of the invention are oligonucleotides whose structure enables them to form oligonucleotide multimer aggregates with the target oligonucleotide, but not with the failure sequences. The aggregates containing the fall length oligonucleotide can then be separated from the unbound failure sequences using standard size exclusion chromatographic techniques. The methods of the invention comprise the purification procedure using the oligonucleotides of the invention.

In one aspect of the invention, oligonucleotides according to the invention (herein called "multimeric oligonucleotides") have three distinct structural domains: i) a multimerization domain, ii) a flexible linker, and iii) a hybridization domain. In one embodiment of this aspect of the invention, the multimerization domain is a sequence of 4–10 nucleotides that, when present in a longer oligonucleotide, results in the oligonucleotide aggregating into multimers, hence the name "multimerization domain." Nucleotide sequences containing four or more contiguous guanine (G) residues form multimeric structures known as G-DNA or tetraplex DNA. Sen and Gilbert, *Nature* 364, 334 (1988). Consequently, in one embodiment of the invention, the multimerization domain is a short sequence of G nucleotides, generally about 4 to 10 nucleotides. The multimerization domain may contain interruptions of the G nucleotide sequence by one or two A or U nucleotides, provided that the ability of the multimerization domain to induce tetraplex formation is not defeated, which generally means that it contains at least 4 contiguous G nucleotides. Preferably, from one to all of the G nucleotides is 2'-substituted with a tetraplex-stablizing substituent. A number of such 2'-substituents are known to those skilled in the art and include, for instance, —$N_3$, —F, —Cl, and —OR where R is methyl, ethyl, propyl, allyl, and methoxyethoxy. Such substitutions increase the stability of the interoligonucleotide tetraplex formed by the multimerization domain.

A nucleotide or non-nucleotide linker joins multimerization and hybridization domains and facilitates independent multimerization and hybridization events. The linker can be a nucleotide linker of 2 to 10 nucleotides that are not complementary to the multimerization or hybridization domains (to prevent hybridization between the linker and either of these domains). The linker can also be a non-nucleotide linker of 2 to 15 constituent members such as, but not limited to, ethylene glycol, tri(ethylene glycol), tetra (ethylene glycol), penta(ethylene glycol) and hexa(ethylene glycol). Other suitable linkers are known in the art, some of which are described in U.S. Pat. Nos. 5,321,131, 5,536,821, and 5,510,471.

The hybridization domain consists of a sequence of about 6 to 15 nucleotides that is complementary in the Watson-Crick sense to one of the ends of an antisense oligonucleotide whose purification is desired (e.g., for example, oligonucleotide sequence SEQ ID NO 4, infra). Alternatively, the hybridization domain may comprise peptide nucleic acids (PNAs) having a sequence complementary to the target nucleic acid. See Nielson et al. (*J. Mol. Recognition* 7, 165 (1994)) for a discussion of PNAs. Although we generally recite oligonucleotides and nucleic acids in the hybridization domain as well as being targets, it will be appreciated by those skilled in the art that the hybridization domain, target, or both can be PNAs.

Alternatively, in this aspect of the invention, the multimeric oligonucleotides can comprise a single multimerization domain with a linker domain and corresponding hybridization domain on both the 3' and 5' end. In this embodiment the multimerization domain can be 4 to 15 nucleotides long (preferably 10–15) and is further defined as before. The linker and hybridization domains are as defined above. The two linkers and the two hybridization domains of each multimeric oligonucleotide can be the same or different.

Oligonucleotides according to the invention can be modified in the base, sugar, or internucleoside linkage as desired for the particular application, e.g., to increase binding affinity. Essentially any modification is acceptable so long as it does not prevent the oligonucleotide from performing its designated function. A number of such modification are known to those skilled in the art. Agrawal and Iyer (*Current Opin. Biotech.* 6, 12 (1995)) review a number of these modifications. See also Uhlmann and Peyman (*Chem. Rev.* 90, 543. (1990)).

Figure 2:
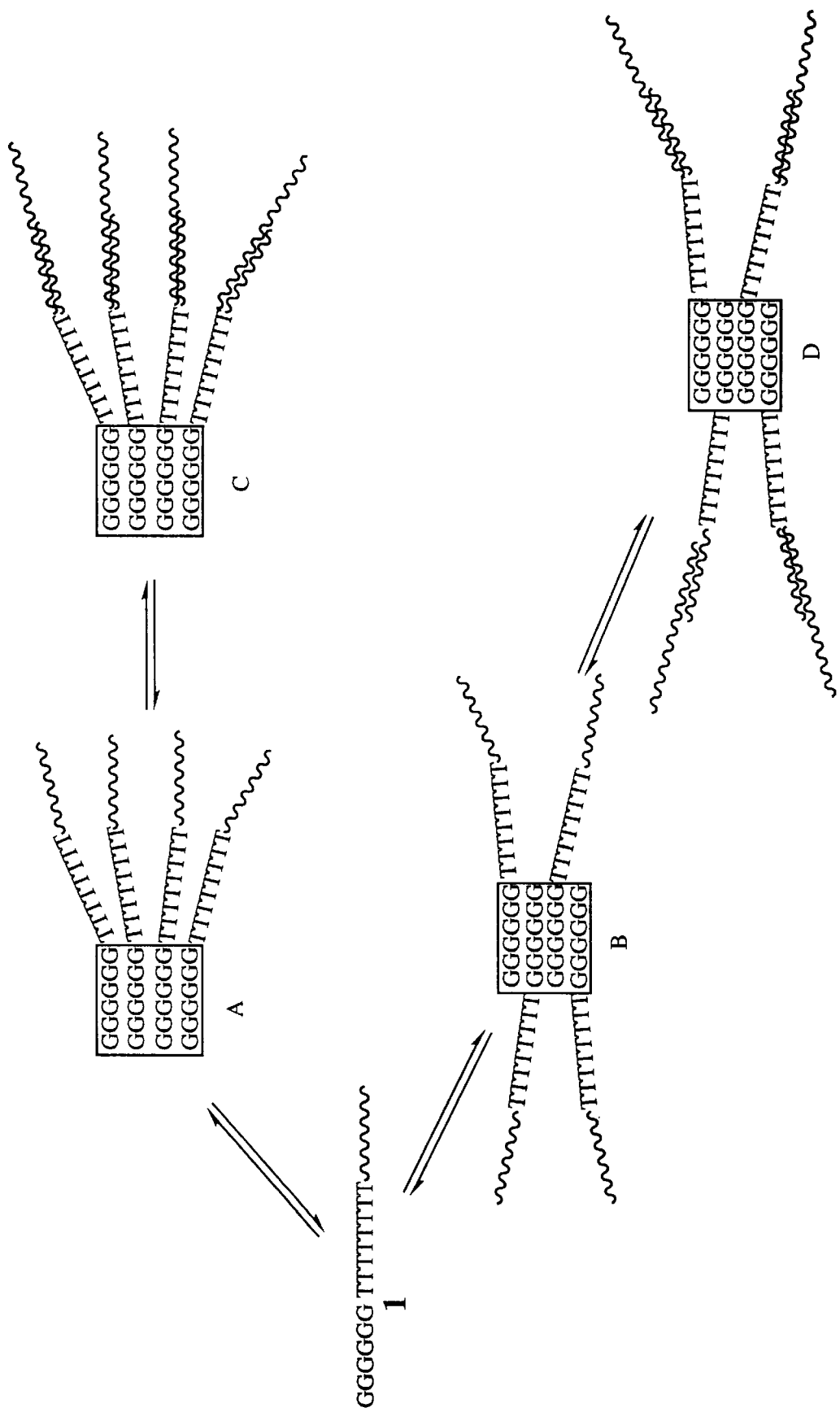
FIG. 2 displays the multimerization of oligonucleotide SEQ ID NO 1 (structures A and B) and the corresponding aggregate with antisense oligonucleotide SEQ ID NO 4 (structures C and D).

The concept underlying this aspect of the invention is schematically displayed in FIG. 2. The multimerization domains of several multimeric oligonucleotides become associated through mutual interactions (e.g., Hoogsteen base pairing in the case of oligonucleotide (G) multimerization domains). This brings several of multimeric oligonucleotides together to form an oligonucleotide aggregate (structures A and B of FIG. 2). When a solution of synthetic oligonucleotides having a sequence complementary to the hybridization domain of the multimeric oligonucleotides is added, the synthetic oligonucleotides hybridize to the hybridization domain of the multimeric oligonucleotides via Watson-Crick base pairing. Conditions are selected so that N-1 and other failure sequences having fewer bases complementary to the multimeric oligonucleotides' hybridization domain do not hybridize to the multimeric oligonucleotides. The appropriate conditions will depend on a number of factors, including target nucleic acid length and sequence. It is a routine matter to adjust the temperature, salt concentration (ionic strength), and pH of the buffer to obtain the desired stringency and, consequently, selectivity. The result is that the target oligonucleotide becomes part of a large oligonucleotide aggregate (structures C and D in FIG. 2), whereas the synthetic oligonucleotide failure sequence remain in solution as individual (i.e., unassociated) molecules. The oligonucleotide aggregates containing the target oligonucleotide are then separated from the synthetic failure sequences using standard size exclusion chromatography (e.g., sephadex or sephacryl columns) under conditions selected to maintain the integrity of the aggregates. Once again, the conditions (pH, temperature, salt concentration) are application dependent but can be adjusted in a routine manner to obtain the desired result. A schematic depiction of the process is displayed in FIG. 7.

As can be appreciated from the foregoing, the linker domain serves to distance the hybridization domain of the multimeric oligonucleotides from the aggregated multimerization domain core of the oligonucleotide, making the hybridization domain appear to its binding partner (i.e., the complementary target oligonucleotide) like an individual oligonucleotide free in solution. Detrimental interactions with the multimer core of the aggregate is thereby avoided, facilitating hybridization of the synthetic oligonucleotide to the hybridization domain.

Oligonucleotides according to this aspect of the invention can be synthesized using standard techniques. E.g., *Methods in Molecular Biology,* Vol. 20, supra.

Another aspect of the invention is the aggregates formed by the multimeric oligonucleotides. These aggregates generally comprise four or more multimeric oligonucleotides that self-associate via the multimerization domains. See, e.g., Sen and Gilbert et al.

In another embodiment, the multimerization domain is a non-nucleotide chemical moiety that contains several (about 2 to 20) amino, hydroxyl, or carboxyl functional groups (including combinations thereof) that permit attachment of hybridization domain(s) (as defined above) to the multimerization domain with or without a linker. In this aspect, the present invention provides oligonucleotide dendrimers. Oligonucleotide dendrimers generally comprise two or three components: a chemical core, optionally a linker domain, and from 2 to about 16 hybridization domains. The linker domains and the hybridization domains of the oligonucleotide dendrimers are the same as defined previously for the multimeric oligonucleotides. The oligonucleotides of the oligonucleotide dendrimers are linked to the chemical core either directly or through the linker domain. Two types of oligonucleotide dendrimers are displayed in FIG. 3. As can be appreciated from FIG. 3 and the purpose for which the oligonucleotide dendrimers are intended, the oligonucleotides of the oligonucleotide dendrimers are preferably linked to the chemical core (directly or through a linker) in such a manner as to make them accessible in solution for hybridization to the desired oligonucleotide.

As noted, the oligonucleotides of the oligonucleotide dendrimers have a hybridization domain that is complementary to the oligonucleotide to be purified or detected. This hybridization domain can comprise the entire oligonucleotide or only a portion thereof. In either instance, the hybridization domain need only be sufficiently long so as to specifically hybridize to the oligonucleotide of interest under acceptable conditions. The only other structural constraint on the oligonucleotide dendrimers is that they do not have any modifications or other features that would interfere with their principal function, i.e., hybridizing with complementary oligonucleotides in solution.

Based upon the foregoing discussion and the theme depicted in FIG. 3, those skilled in the art will appreciate that a wide variety of dendrimer structures fall within the spirit and scope of the present invention, and any such structure can be used in the invention so long as it conforms to the requirements set forth herein, including that it is water soluble. A number of suitable dendrimeric structures are known. E. g., Newkome et al., *Aldrichemica Acta* 25, 31(1992).

Figure 3A:
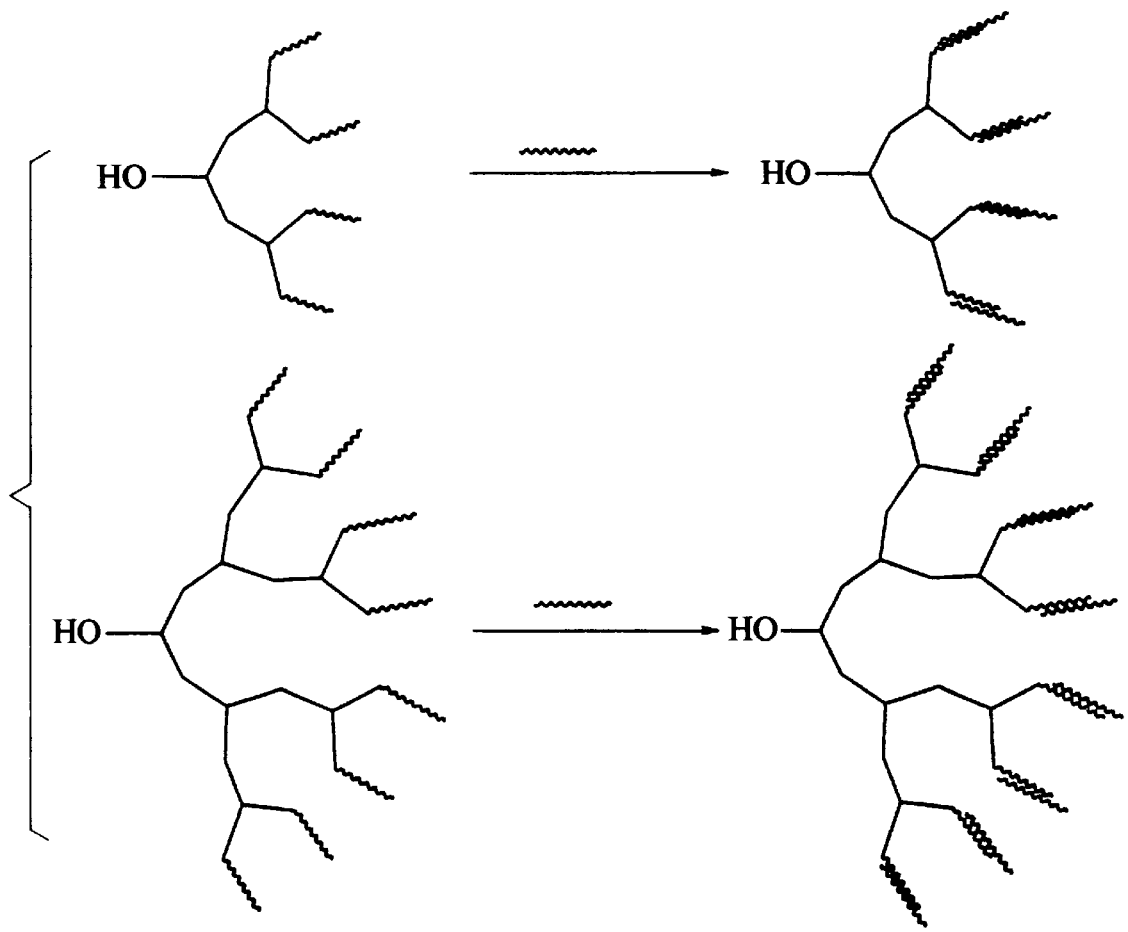
FIG. 3A displays two representative oligonucleotide dendrimers of the invention with 4 and 8 branches and their hybridization with an oligonucleotide, and FIG. 3B displays a representative STARBURST™ molecule with 12 arms and its conjugate aggregate with SEQ ID NO 4.

A preferred oligonucleotide dendrimer of the invention is a branched dendrimer, an example of which is shown in FIG. 3A. Such dendrimers are synthesized using branching CPG solid support and branching phosphoramidites. For instance, such oligonucleotide dendrimers can be synthesized on CPG (2000 or 3000 Å pore size) (see Example 1, infra) attached to 1,3-didimethoxytrityl-2-glycerol. Symmetric branching phosphoramidite for use in the synthesis is commercially available (e.g, Clontech, Palo Alto, Calif.). By this method one can control the number of branches required to the range of 2–16.

Figure 3B:
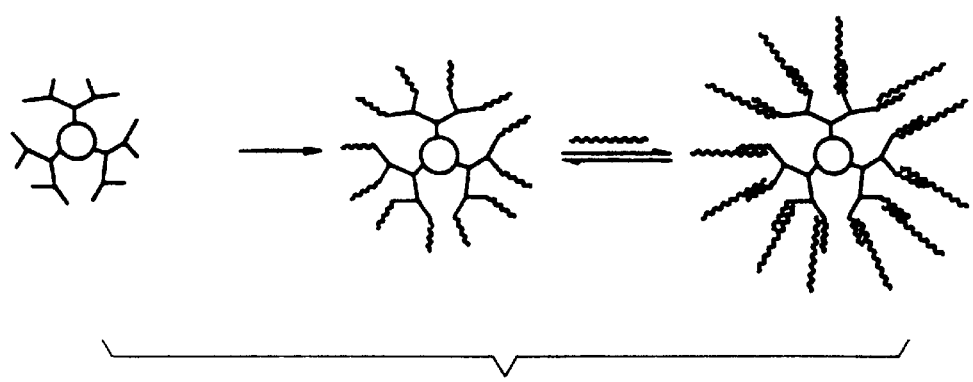

Another preferred oligonucleotide dendrimer of the invention is a STARBURST™ dendrimer, as shown in FIG. 3B. STARBURST™ dendrimers are synthesized by conjugating STARBURST™ (PAMAM) dendrimer (Aldrich, Milwaukee, Wis.) with oligonucleotide sequences (linker and hybridization domains) using the chemistry shown in FIG. 6. Any generation STARBURST™ dendrimer can be used so long as the oligonucleotide dendrimer is water soluble.

Other dendrimers suitable for use in the present invention include Star PEGs and Branched PEGs (PEG=polyethylene glycol), commercially available from Shearwater Polymers, Inc. (Huntsville, Ala.). These are multi-armed PEGs made by polymerization of ethylene oxide from a cross-linked divinyl benzene core. Gnanou et al., *Makromol. Chem.* 189, 2885 (1988); Rein et al., *Acta Polymer* 44, 225 (1993). Still other dendrimeric molecules useful in the invention can be synthesized according to the methods of Rein et al. (*Acta Polymer* 44, 225 (1993)) and references cited therein, and Merrill (U.S. Pat. No. 5,171,264), both of which disclose polyethylene oxide star molecules.

Figure 6:
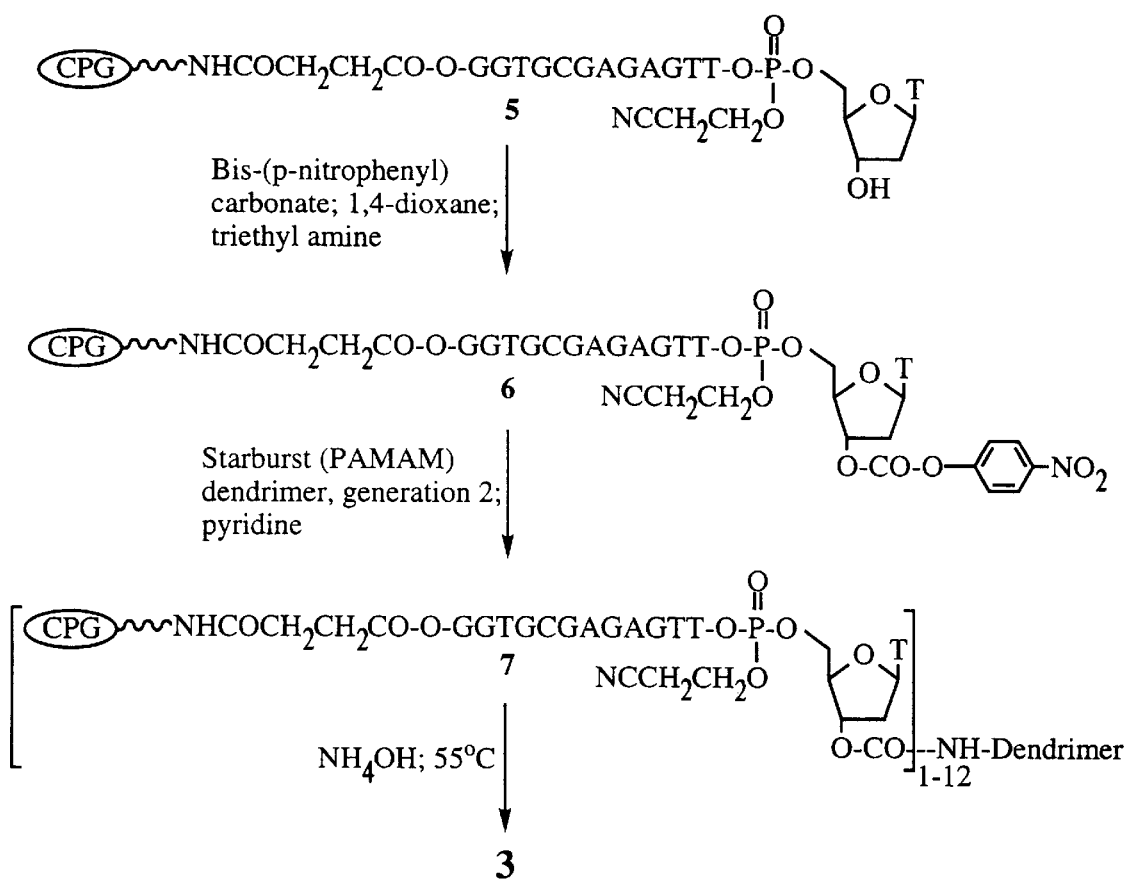
FIG. 6 displays a schematic representation of the method of synthesizing dendrimer oligonucleotides according to the invention. The STARBURST™ dendrimer is displayed as a representative example.

Oligonucleotide dendrimers according to the invention can be synthesized with other than the STARBURST™ dendrimer using the protocol outlined in FIG. 6 with only minor modifications.

In another aspect, the invention comprises methods of separating, purifying, and detecting oligonucleotides. In one embodiment of this aspect of the invention, the method comprises contacting a solution containing an oligonucleotide whose separation, purification, or detection is desired with multimeric oligonucleotides or oligonucleotide dendrimers of the invention having a hybridization domain sufficiently complementary to the desired oligonucleotide to specifically hybridize to the desired oligonucleotide (but not to other oligonucleotides having similar sequences) under the conditions selected. After hybridization has taken place, the solution is subjected to size exclusion chromatography with an elution buffer selected to maintain the integrity of the aggregates. The elution buffer temperature, pH, and salt concentration are application dependent but routine to determine. The fraction containing the multimeric oligonucleotide aggregates to which the desired oligonucleotide is bound will generally be the fastest moving component on the column. Detection is done at standard wavelengths, and the fraction containing the first component off the column is collected. The aggregate-containing fraction is subject to a buffer that causes the target oligonucleotide to disassociate from the multimeric oligonucleotide or oligonucleotide dendrimer and then separated by size exclusion chromatography. As before, suitable buffer conditions are arrived at through routine adjustment of temperature, ionic strength and pH. Two fractions are collected, one containing the purified target oligonucleotide and one containing the multimeric oligonucleotide or oligonucleotide dendrimer (whichever is used). The multimeric oligonucleotide or oligonucleotide dendrimer can then be reused for additional purifications.

As an alternative to size exclusion chromatography, the present methods can be conducted with a small pore filter membrane such as micricon and centricon filters available from Amicon (Beverly, Mass.), which are particularly useful for small scale purification like those in which PCR is used. Membrane filter cartridges or pumps with suitable pore sizes can be used for large scale purification. Such filter membranes of course will have a pore size chosen to allow unbound failure sequences to pass through but not the multimeric oligonucleotide (or oligonucleotide dendrimer)/ target nucleic acid aggregate. In this aspect of the invention, the solution containing the aggregate and failure sequences is filtered through the membrane. As before, the solution buffer is chosen to be of such stringency as to allow selective hybridization of the target sequence but not other oligonucleotides to the hybridization domain. The filtrate (containing the failure sequences) can be discarded if desired. The material remaining on the filter, which is the aggregate, is then washed in situ with a buffer having a stringency that causes the target to disassociate from the oligonucleotide multimer or dendrimer oligonucleotide. The unbound target oligonucleotide will pass through the membrane. The filtrate containing the isolated oligonucleotide is collected. The membrane, on which the oligonucleotide multimer or dendrimer oligonucleotide is, can be washed and the oligonucleotide multimer or dendrimer oligonucleotide collected and used again.

The present compounds and methods can also be used to isolated segments from a genome. In this aspect of the invention the hybridization domain of the multimeric oligonucleotide or oligonucleotide dendrimer is complementary in the Watson-Crick, Hoogsteen, reverse Watson-Crick, or reverse Hoogsteen sense. The genome or portion thereof containing the segment of interest (the target segment) is subject to restriction endonucleases and the resulting hydrolysate subject to the methods of the invention. If the target segment is purine rich, the hybridization domain of the multimeric oligonucleotide or oligonucleotide dendrimer may be complementary in the Hoogsteen or reverse Hoogsteen sense to the purine rich segment so that the double stranded target segment hybridizes to the hybridization domain to form a triplex. Alternatively, where the target segment is a mixed sequence of purine and pyrimidines, it is preferably denatured first and the hybridization domain is complementary in the Watson-Crick sense to one of the strands.

Figure 7:
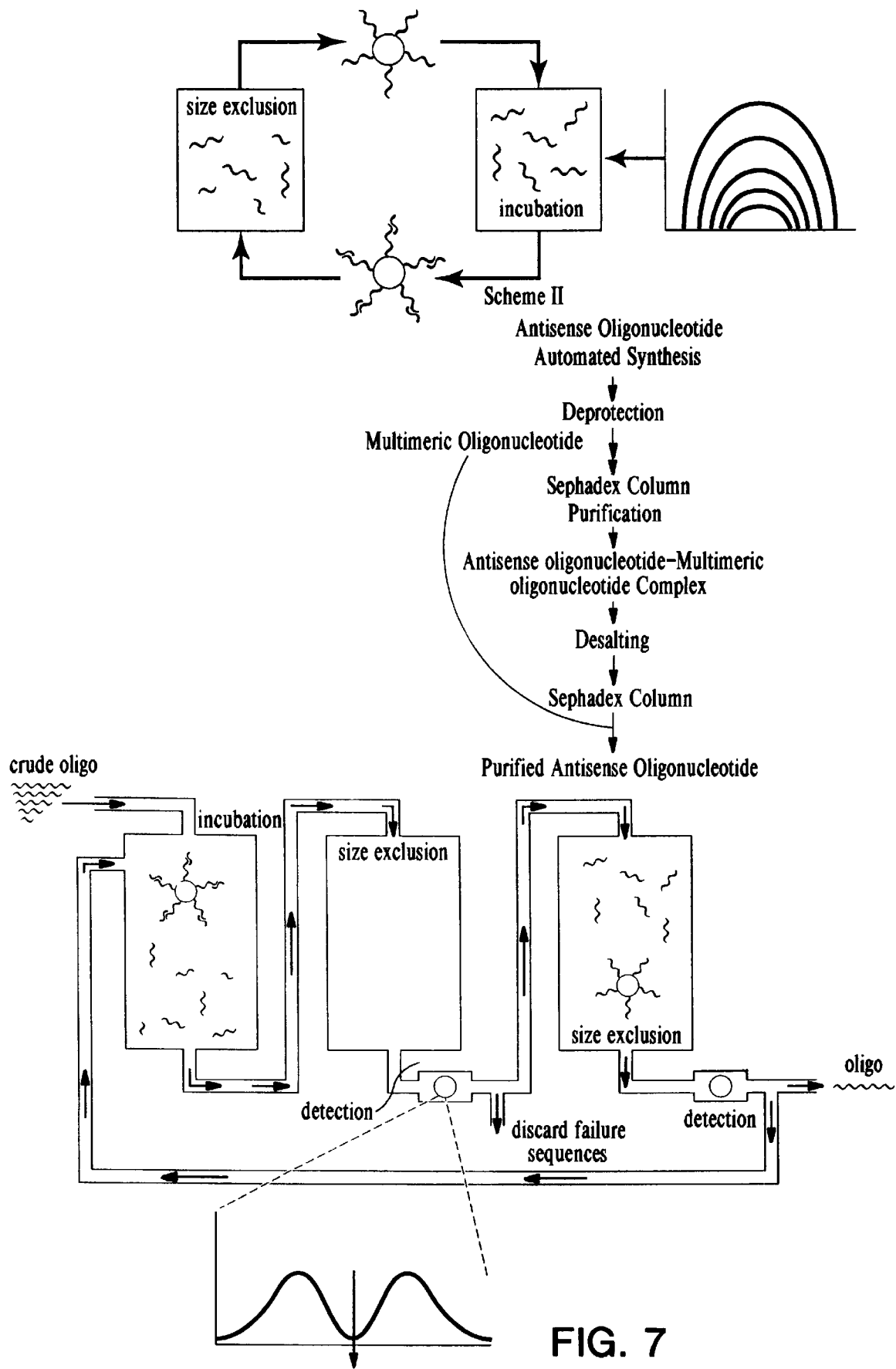
FIG. 7 displays a schematic representation of the method according to the invention.

It will be appreciated from the foregoing that the compounds and methods of the invention provide several advantages over prior art techniques. The present methods can be used to purify any molecule capable of specific hybridization based on complementary nucleotide base sequence recognition through Watson-Crick, reverse Watson-Crick, Hoogsteen, or reverse Hoogsteen hydrogen bonding, including but not limited to nucleic acids and PNAs. Most notably, the methods of the invention do not rely on charge, hydrophobicity, or hydrophilicity and, therefore, are suitable regardless of how the target oligonucleotide (or PNA) is modified. An additional advantage of the methods of the invention is that the multimeric oligonucleotide can be used repeatedly for a number of purifications, thereby reducing the cost. The results presented herein demonstrate that the multimeric structures can be used to purify antisense oligonucleotides as shown in FIG. 7.

From the foregoing, those skilled in the art will appreciate that the compounds and methods of the invention are not limited to isolating a single synthetic oligonucleotide from a mixture of failure sequences, but can be used to isolate a desired oligonucleotide from any composition in solution. Furthermore, by using compounds of the invention with two or more different hybridization domains or mixtures of the compounds of the invention in which each compound has one of several different hybridization domains, more than one target oligonucleotide can be separated at a time. In this embodiment, multimeric oligonucleotides or asymmetric branching dendrimers (commercially available from, for example, Clontech (Palo Alto, Calif.)) are used.

The following examples are provided for illustrative purposes only and are not intended, nor should they be construed, to limit the invention in any way. Those skilled in the art will appreciate that variations can be made without violating the scope or spirit of the invention.

EXAMPLES

FIG. 1 displays the oligonucleotide sequences and aggregates used in this study. The three boxes (from left to right) in each of the first three structures represent multimeric, linker, and hybridization domains, respectively, as described herein. In dendrimer 2, the number of branches is equal to 2n, and where n is 2–4. In dendrimer 3, the number of branches is equal to n', and where n' is 2–16 (n'=12 is shown in FIG. 3). Oligonucleotide SEQ ED NO 4 is the antisense oligonucleotide whose purification is undertaken, and the underlined portion is complementary to the hybridization domains of oligonucleotide SEQ ID NO 1 and dendrimers 2 and 3.

EXAMPLE 1

Synthetic Methods

Oligonucleotide Synthesis

Oligonucleotides were synthesized on a Milligen 8700 DNA synthesizer (Bedford, Mass.) using phosphoramidite chemistry. P-cyanoethyl-N,N-diisopropyl phosphoramidites were purchased from Millipore for DNA synthesis. Oligonucleotide SEQ ID NO 2 was synthesized on CPG (2000 or 3000 Å pore size) attached to 1,3-didimethoxytrityl-2-glycerol. Symmetric branching phosphoramidite was obtained from Clontech (Palo Alto, Calif.). After attaching the required number of branches on the synthesizer, oligonucleotide synthesis was continued with normal P-cyanoethyl-N,N-diisopropyl phosphoramidites as described above.

After synthesis, oligonucleotides SEQ ID NOs 1 and 2 were deprotected, purified on reverse phase HPLC ($C_{18}$), detritylated, and desalted using $C_{18}$ Sep-pack cartridges (Waters, Milford, Mass.). Oligonucleotide SEQ ID NO 4 was deprotected and used as is without purification.

Synthesis of Branching Dendrimer

We synthesized 1,3-di-dimethoxytrityl-2-hydroxy-glycerol by treating glycerol with 2 equivalents of 1,1'-dimethoxytrityl chloride (DMTCl) in pyridine for 24 hrs at room temperature and for additional 7 hrs at 50° C. to allow completion of the second hydroxy group with DMTCl. The di-DMT-2-hydroxy glycerol was purified by flash column chromatography on silica gel 60 (<230 mesh ASTM, Merck, Darmstadt, Germany) by eluting with a mixture of hexane:methylene chloride:triethylamine (20:4:1). Yield of the purified white diDMT product was 94%.

The diDMT product obtained was loaded on to long chain alkylamido propionic acid controlled-pore glass (CPG) supports (CPG, Inc., Lincoln Port) having pore sizes of 2000 and 3000 Å as reported (Damha et al., *Nucleic Acids Res.* 18, 3813 (1990)) to yield 1,3-diDMT-2-hydroxy-glycerol on CPG. The loading efficiencies were 13.8 µmoles/gm (2000 Å) and 9.3 µmoles gm (3000 Å).

Conjugation of Oligonucleotide to STARBURST™ Dendrimer

The 3 '-DMT-5'-P-cyanoethyl-N,N-diisopropyl phosphoramidites and 5'-monomer attached CPG solid support were obtained from Glen Research Laboratories (Sterling, Va.) or Chemgenes (Waltham, Mass.). Dendrimer 5 (FIG. 6) was synthesized on a 5'-monomer attached CPG using 3'-DMT-5'-phosphoramidite monomers with longer detritylation coupling times and in trityl-off mode. Then the CPG-attached oligonucleotide with free 3'-OH was activated with bis(p-nitrophenyl) carbonate in anhydrous 1,4-dioxane with triethylamine as catalyst (3 drops) for 1 hr to obtain active carbonate dendrimer 6 (FIG. 6) as described by Habus et al. (*Bioorganic and Med Chem. Lett.* 4, 1065 (1994)) and Habus et al. (*Bioconjugate Chem.* 6, 327 (1995)). The active oligonucleotide carbonate was then successively washed with anhydrous 1,4-dioxane and acetonitrile and dried in vacuum. The activated oligonucleotide was taken in anhydrous pyridine/methanol and added to STARBURST™ (PAMAM) dendrimer, generation 2 (Mol. Wt. 3,256) (Aldrich Chemical Co. Milwaukee) and shaken in a mechanical shaker for 2 hrs at room temperature to give dendrimer 7 (FIG. 6). Then the product was washed with pyridine and methanol. Dendrimer 3 (FIG. 1) was cleaved from CPG and deprotected as described above. Then the aggregate was purified on polyacrylamide gel.

EXAMPLE 2

Purification With Multimeric Oligonucleotides

Crude oligonucleotide SEQ ID NO 4 was labeled at the 5'-end with $^{32}$P using T4-polynucleotide kinase (Promega, Madison, Wis.), and γ-$^{32}$P-dATP (Sambrook et al., *Molecular Cloning* (Cold Spring Harbor Press, Cold Spring Harbor, N.Y., 1989.)). Tetraplex (multimeric structure) formation was confirmed on gel using 5'-end $^{32}$P labeled oligonucleotide SEQ ID NO 1 in 200 mM potassium acetate. For purification experiments, the required amount of labeled, cold oligonucleotide SEQ ID NO 4 was mixed with oligonucleotides SEQ ID NO 1 in 10 mM sodium dihydrogen phosphate (pH 7.6) and 100 mM sodium chloride and incubated for 30–60 min. Then the samples were loaded on 20% non-denaturing polyacrylamide gel and electrophoresed. The slow moving band was excised from the gel and eluted with 0.5 mM sodium acetate (pH 7.2) overnight and ethanol precipitated. The DNA sample was then mixed with formamide gel loading buffer and analyzed on a denaturing 7M urea polyacrylamide gel.

Figure 4A:
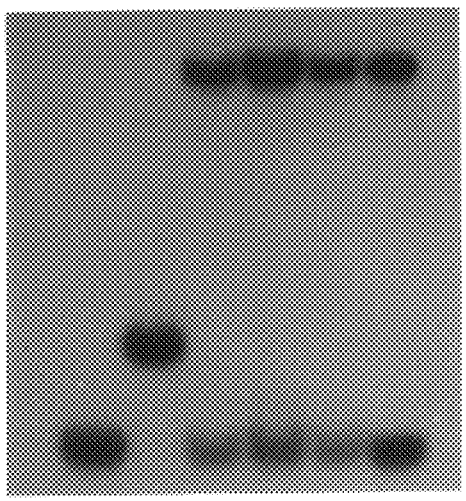
FIG. 4A displays an autoradiogram of non-denaturing polyacrylamide gel showing multimeric structures formed with SEQ ID NO 1, and FIG. 4B displays an autoradiogram showing homogeneity of SEQ ID NO 4 purified with multimeric oligonucleotide SEQ ID NO 1.

FIG. 4A is an autoradiogram of non-denaturing polyacrylamide gel showing multimeric structures formed with oligonucleotide SEQ ID NO 1. Lanes 1 and 2 are markers of 22-base long single- and double-stranded DNAs, respectively. Lanes 3–6 contain oligonucleotide SEQ ID NO 1 incubated in 100 mM NaOAc, pH 7.6 (lane 3), 200 mM NaOAc, pH 7.6 (lane 4), 100 mM KOAc, pH 7.6 (lane 5), and 200 mM KOAc, pH 7.6 (lane 6). The figure shows that SEQ ID NO 1 forms multimeric structure (tetraplex) as expected.

Figure 4B:
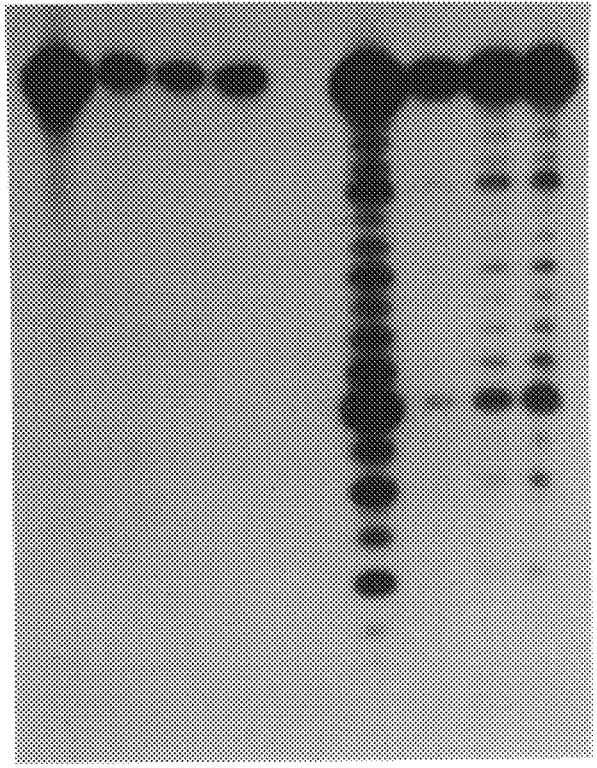

FIG. 4B is an autoradiogram showing homogeneity of SEQ ID NO 4 purified with multimeric oligonucleotide SEQ ID NO 1. Lanes 5 and 6 are crude SEQ ID NO 4 before and after treating with SEQ ID NO 1. Lane 1 is purified SEQ ID NO 4 by standard methods. Lanes 2–4 are SEQ ID NO 4 prepurified by conventional techniques and subsequently treated with SEQ ID NO 1 as in the case of crude SEQ ID NO 4. This figure shows that the isolated fraction contains only pure antisense oligonucleotide SEQ ID NO 1 (lanes 2, 3, 4, and 6) (compare with lanes 1 and 5, which contain purified and crude oligonucleotide SEQ ID NO 4, respectively).

EXAMPLE 3

Purification With Oligonucleotides Dendrimers

We used oligonucleotide dendrimers shown in FIG. 3A to demonstrate their use for purification of antisense oligonucleotide SEQ ID NO 4. Dendrimer 2 (FIG. 1) was used for purification in the same manner as SEQ ID NO 1, as described in Example 2.

Figure 5A:
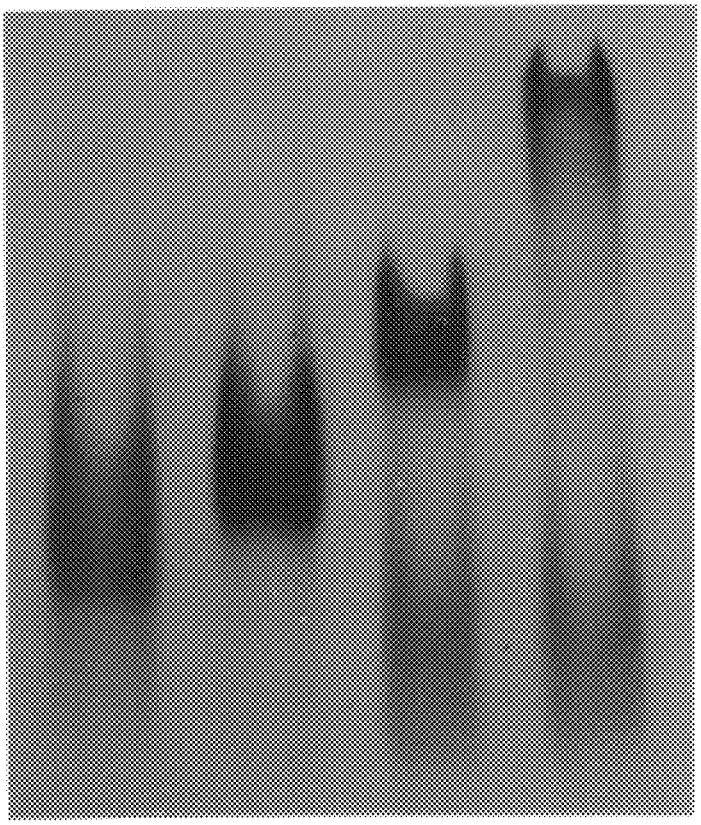
FIG. 5A displays an autoradiogram of a non-denaturing gel showing the mobility of crude SEQ ID NO 4 alone and as part of a complex, and FIG. 5B displays an autoradiogram of a denaturing gel showing homogeneity of the bands excised from the autoradiogram of FIG. 5A.
Figure 5B:
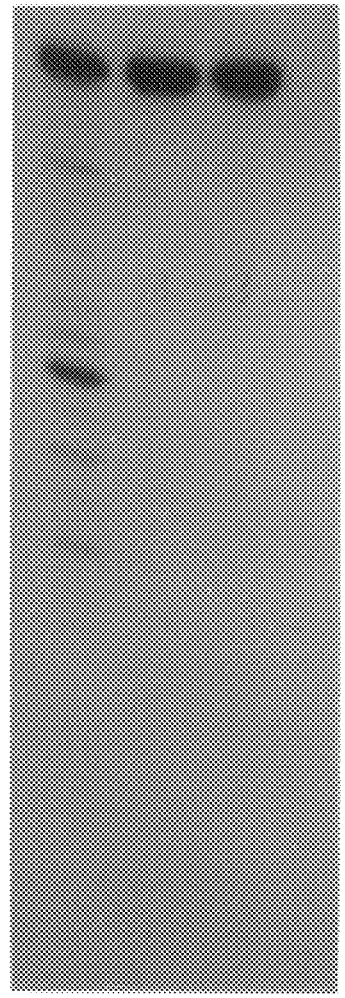

FIG. 5A is an autoradiogram of a non-denaturing gel showing the mobility of the complexes of crude SEQ ID NO 4 with 2 and 4 branched dendrimer 2 (FIG. 1) (lanes 3 and 4, respectively). Lane 1 is crude SEQ ID NO 4 alone. Lane 2 is crude SEQ ID NO 4 with a 25 base long complementary sequence. Note that the failure sequences are seen as a diffuse band below the dark band in lane 1, not seen in lane 2, but present in lanes 3 and 4. Appropriate bands were cut, eluted, and run on a denaturing polyacrylamide gel to examine the homogeneity of oligonucleotide SEQ ID NO 4. FIG. 5B is an autoradiogran of a denaturing gel showing homogeneity of the bands excised from lanes 2 (lane 1), 3 (lane 2) and 4 (lane 3) of the gel shown in FIG. 5A. Lanes 2 and 3 of FIG. 5B suggest that the oligonucleotide is pure and the failure sequences are absent. Similar results obtained with the oligonucleotide dendrimer shown in FIG. 3B.

---

We claim:

1. A multimeric oligonucleotide consisting of a multimerization domain, a hybridization domain, and a linker domain, wherein the multimerization domain is an oligonucleotide of from 4 to 10 nucleotides in which at least 4 contiguous nucleotides are G nucleotides, the hybridization domain is an oligonucleotide of from about 6 to about 15 nucleotides complementary to another nucleic acid, and the linker domain connects the multimerization domain and the hybridization domain and is an oligonucleotide of from about 2 to about 10 nucleotides or a non-nucleotide chemical moiety selected from the group consisting of the terminal diradicals of ethylene glycol, tri(ethylene glycol), tetra(ethylene glycol), penta(ethylene glycol), hexa(ethylene glycol) and the diradicals —NH(CH$_2$)$_n$NH—, wherein n is 2, 3, 4, 5, or 6 and failure sequences thereof.

2. A method of purifying a target oligonucleotide or peptide nucleic acid (PNA) comprising contacting the target oligonucleotide with a multimeric oligonucleotide according to claim 1 under conditions in which the hybridization domain specifically hybridizes to the target to form a multimeric oligonucleotide/target oligonucleotide aggregate, separating the aggregate from the mixture of oligonucleotides, disassociating the target oligonucleotide from the aggregate, and separating the target oligonucleotide from multimeric oligonucleotide.

3. An aggregate comprising four or more oligonucleotides according to claim 1.

4. The oligonucleotide according to claim 1 wherein one or more of the G nucleotides has a tetraplex-stablizing 2'-substituent, selected from the group consisting of —N$_3$, —F, —Cl, and —OR, wherein R is methyl ethyl, propyl, allyl, and methoxyethoxy and n is 2, 3, 4, 5, or 6.

5. An aggregate comprising four or more oligonucleotides according to claim 4.

6. A method of purifying a target oligonucleotide or peptide nucleic acid (PNA) comprising contacting the target with a multimeric oligonucleotide according to claim 4 under conditions in which the hybridization domain specifically hybridizes to the target to form a multimeric oligonucleotide/target oligonucleotide aggregate, separating the aggregate from the mixture of oligonucleotides, disassociating the target oligonucleotide from the aggregate, and separating the target oligonucleotide from multimeric oligonucleotide.

7. The oligonucleotide according to claim 4 wherein the linker domain consists of from about 2 to about 10 nucleotides.

8. An aggregate comprising four or more oligonucleotides according to claim 7.

9. A method of purifying a target oligonucleotide or PNA comprising contacting the target with a multimeric oligonucleotide according to claim 7 under conditions in which the hybridization domain specifically hybridizes to the target to form a multimeric oligonucleotide/target oligonucleotide aggregate, separating the aggregate from the mixture of oligonucleotides, disassociating the target oligonucleotide from the aggregate, and separating the target oligonucleotide from multimeric oligonucleotide.

10. The oligonucleotide according to claim 4 wherein the linker domain consists of from about 2 to about 15 non-nucleotide chemical moieties selected from the group consisting of the terminal diradicals of ethylene glycol, tri(ethylene glycol), tetra(ethylene glycol), penta(ethylene glycol), and hexa(ethylene glycol).

11. A method of purifying a target oligonucleotide or peptide nucleic acid (PNA) comprising contacting the target with a multimeric oligonucleotide according to claim 10 under conditions in which the hybridization domain specifically hybridizes to the target to form a multimeric oligonucleotide/target oligonucleotide aggregate, separating the aggregate from the mixture of oligonucleotides, disassociating the target oligonucleotide from the aggregate, and separating the target oligonucleotide from multimeric oligonucleotide.

12. An aggregate comprising four or more oligonucleotides according to claim 10.

13. A multimeric oligonucleotide consisting essentially of a multimerization domain, two hybridization domains, and two linker domains, wherein the multimerization domain is an oligonucleotide of from 4 to 10 nucleotides in which at least 4 contiguous nucleotides are G nucleotides, the hybridization domains are independently oligonucleotides of from about 6 to about 15 nucleotides independently complementary to the same or different nucleic acids, and the two linker domains connect the multimerization domain and the hybridization domains and are independently oligonucleotides of from about 2 to about 10 nucleotides or a non-nucleotide chemical moieties selected from the group consisting of the terminal diradicals of ethylene glycol, tri(ethylene glycol), tetra(ethylene glycol), penta(ethylene glycol), hexa(ethylene glycol), and the diradicals —NH(CH$_2$)$_n$NH—, wherein n is 2, 3, 4, 5, or 6 and failure sequences thereof.

14. A method of purifying a target oligonucleotide or PNA comprising contacting the target with a multimeric oligonucleotide according to claim 13 under conditions in which the hybridization domains specifically hybridize to the target to form a multimeric oligonucleotide/target oligonucleotide aggregate, separating the aggregate from the mixture of oligonucleotides, disassociating the target oligonucleotide from the aggregate, and separating the target oligonucleotide from multimeric oligonucleotide.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 22 base pairs

```
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:1:

TGCGAGAGTT TTTTTTGGGG GG                                              22

(2) INFORMATION FOR SEQ ID NO:2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:2:

GGTGCGAGAG TTT                                                        13

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:3:

TTTTTTTTGG GGGG                                                       14

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:4:

CTCTCGCACC CATCTCTCTC CTTCT                                           25
```